United States Patent
Moy et al.

(10) Patent No.: US 6,303,052 B1
(45) Date of Patent: *Oct. 16, 2001

(54) ANTIOXIDANT COMPOSTIONS

(75) Inventors: Shirley A. Moy; Kurt W. McWilliams, both of Austin, TX (US)

(73) Assignee: Condea Vista Company, Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/260,775

(22) Filed: Mar. 2, 1999

(51) Int. Cl.$^7$ .................................................. C09K 15/00
(52) U.S. Cl. ............................ 252/397; 560/67; 560/75; 560/103; 560/105
(58) Field of Search ..................... 560/103, 105, 560/67, 75; 252/397

(56) References Cited

U.S. PATENT DOCUMENTS

| | | | |
|---|---|---|---|
| 3,285,855 | 11/1966 | Dexter et al. | 510/141 |
| 3,330,859 | 7/1967 | Dexter et al. | 546/217 |
| 3,681,431 | 8/1972 | Dexer et al. | 560/75 |
| 4,228,297 | 10/1980 | Haeberli et al. | 560/75 |
| 5,523,007 | * 6/1996 | Kristen et al. | 508/297 |
| 5,696,281 | 12/1997 | Evans | 560/67 |
| 5,739,341 | 4/1998 | Dubs et al. | 560/75 |
| 5,821,206 | 10/1998 | Payne et al. | 510/141 |

OTHER PUBLICATIONS

Technical Data Sheet 404: Lial 145. Condea Augusta S.p.A., Jun. 1996.
Technical Data Sheet 413: Isalchem 145. Condea Augusta S.p.A., Jun. 1996.

* cited by examiner

Primary Examiner—Gary Geist
Assistant Examiner—Taylor V Oh
(74) Attorney, Agent, or Firm—Browning Bushman

(57) ABSTRACT

An antioxidant composition comprising at least one compound having the formula:

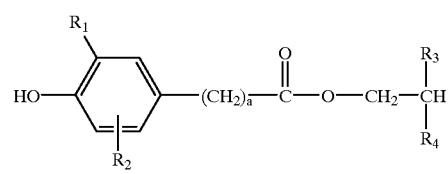

wherein $R_1$ and $R_2$ are each hydrocarbon groups having from 1 to 8 carbon atoms, a is from 1 to 3, $R_3$ is a linear alkyl group having from 4 to 22 carbon atoms, and $R_4$ is a linear alkyl group having from 6 to 24 carbon atoms.

4 Claims, 2 Drawing Sheets

ANTIOXIDANT COMPOSTIONS

BACKGROUND OF THE INVENTION

1. Field of the Invention

The present invention relates to antioxidant compositions and, more particularly, to antioxidant compositions for use in stabilizing host materials containing organic materials.

2. Description of the Prior Art

As noted in U.S. Pat. Nos. 3,330,859; 3,285,855; 4,228,297; 5,696,281; 5,739,341; and 5,821,206, to mention a few, sterically hindered phenols are known stabilizers for host materials—i.e., organic materials or compositions containing organic materials—that are susceptible to thermal, oxidative, and/or actinic degradation. In particular, virtually all polymers, be they synthetic or natural in origin, react with oxygen, such oxidation reactions normally occurring while the polymer is being thermally processed at elevated temperatures. Depending upon the polymer, the oxidation/degradation can manifest itself as discoloration, loss of gloss or transparency, cracked surfaces, loss of mechanical properties such as tensile strength and elongation, etc. In addition to polymers, numerous other host materials such as lubricants, polyols, fuel oils, surfactants, and personal care products—e.g. lotions, creams, etc.—are susceptible to oxidation/degradation, which can affect their appearance and/or effectiveness for their intended usage.

While there are other methods of reducing degradation/oxidation of organic materials or compositions containing organic materials, by far the most common means of achieving this result is by the use of antioxidants, particularly sterically hindered phenols. Hindered phenols exhibiting antioxidant properties can be either liquid or solid in nature, liquid antioxidants possessing the advantage that they are easier to meter into the host material. Regardless of whether the hindered phenols are liquid or solid, thermal stability, resistance to coloration, and purity are important physical properties. Additionally, in the case of liquid antioxidants, physical properties such as liquidity at high molecular weight, low viscosity at low temperatures, low pour points, low volatility, and low freeze points are also important considerations. In particular, the problem that exists to the present time in the antioxidant technology area is the lack of high molecular weight liquid antioxidants that are of high purity, have low freezing points near or below 0° C.—e.g., less than about 5° C. and can be identified/analyzed at low concentrations in the host material. In the latter regard, it will be recognized by those skilled in the art that antioxidants, be they liquid or solid, are typically used at levels below 5,000 ppm. Being used at such low levels, it is important that the level of antioxidant in the host material be easily analyzed so as to ensure that the proper amount of antioxidant is present. By way of example, antioxidants are important polymer additives. If the appropriate amount of antioxidant is not added to polymeric compositions, deleterious effects in the polymer can occur. Such deleterious effects include discoloration, accelerated aging, thermal degradation during production, loss of physical properties, etc.

It therefore would clearly be desirable to have antioxidant compositions that, at low levels, could be accurately analyzed in the host material. It would be especially desirable to have liquid antioxidant compositions that exhibit high purity, low freezing or pour points, and low viscosity at low temperatures.

SUMMARY OF THE INVENTION

It is therefore an object of the present invention to provide antioxidants (antioxidant compositions) of the hindered phenol type that are of high purity.

Another object of the present invention is to provide antioxidant compositions of the hindered phenol type that can be analyzed in a host material at low levels while maintaining good antioxidant efficiency.

Still a further object of the present invention is to provide antioxidant compositions of the hindered phenol type that remains liquid at high molecular weights.

Still a further object of the present invention is to provide antioxidant compositions of the hindered phenol type that are liquid at low temperature, exhibit high purity, and possess a low freezing (pour) point and low viscosity at low temperatures.

The above and other objects of the present invention will become apparent from the description given herein, the drawings, and the appended claims.

The antioxidant compositions of the present invention comprise at least one compound having the formula:

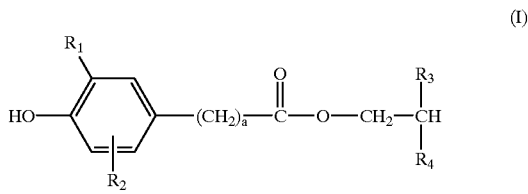

(I)

wherein $R_1$ and $R_2$ are each hydrocarbon groups having from 1 to 8 carbon atoms, a is from 1 to 3, $R_3$ is a linear alkyl group having from 4 to 22 carbon atoms, and $R_4$ is a linear alkyl group having from 6 to 24 carbon atoms. Particularly preferred are compounds having the above formula wherein $R_3$ is a linear alkyl group having from 4 to 10 carbon atoms, and $R_4$ is a linear alkyl group having from 6 to 12 carbon atoms. Compounds having the structure of Formula I wherein the total number of carbons in $R_3$ plus $R_4$ is from 14 to 24 are liquid at temperatures about or below 0° C. and yet possess low volatility so as to be useful under conditions where the host material is subjected to elevated temperatures—e.g., thermal processing of polymeric materials.

DESCRIPTION OF THE PREFERRED EMBODIMENTS

Figure 1:
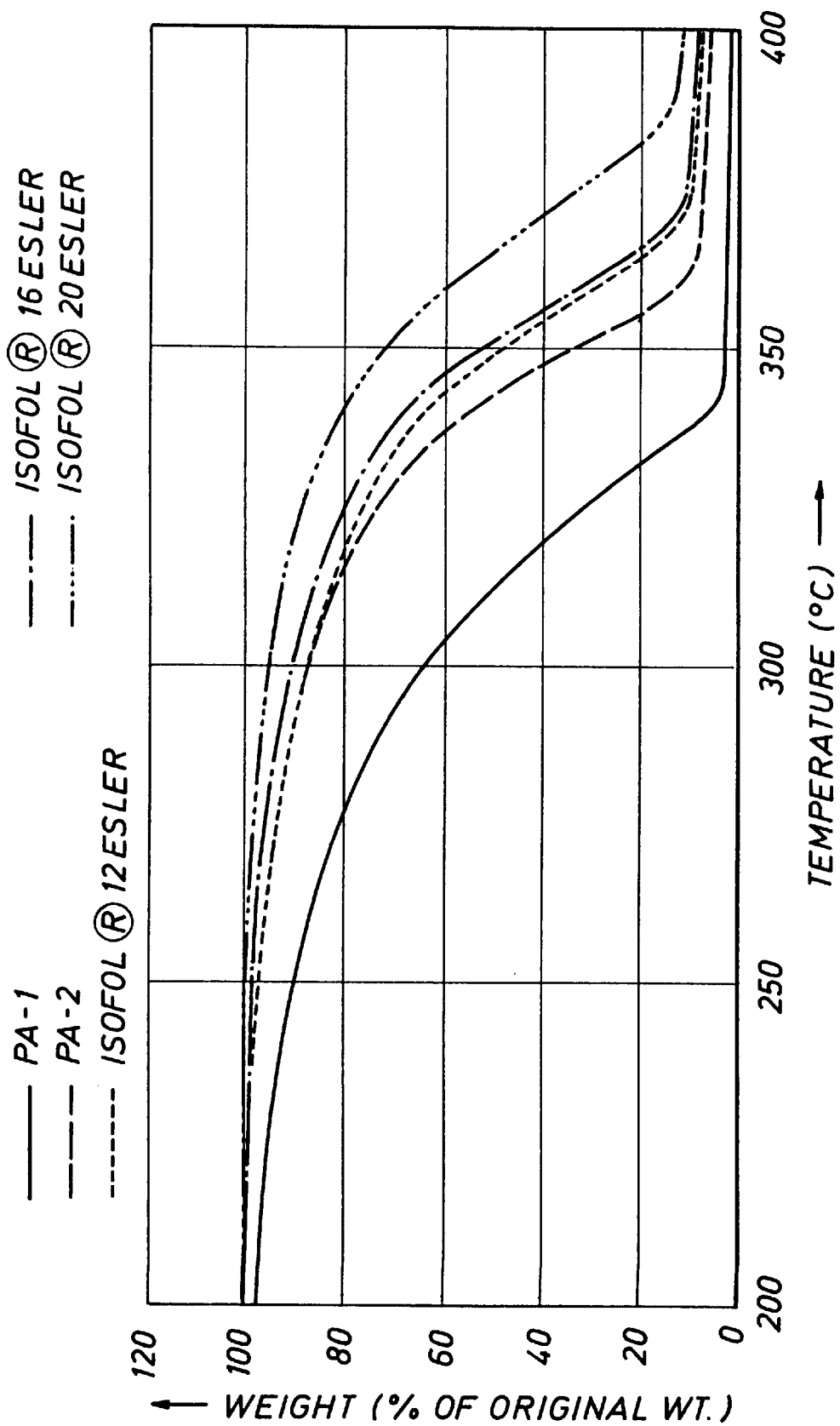
FIG. 1 is a TGA graph comparing the volatility of the antioxidant compositions of the present invention with prior art antioxidant compositions.

The compounds of the compositions of the present invention are represented by the formulas:

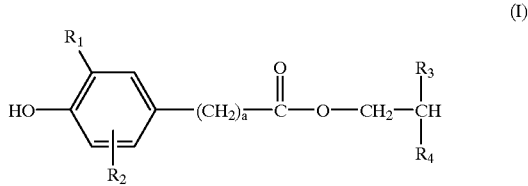

(I)

wherein $R_1$ and $R_2$ are each hydrocarbon groups having from 1 to 8 carbon atoms, a is from 1 to 3, $R_3$ is a linear alkyl group having from 4 to 22 carbon atoms, and $R_4$ is a linear alkyl group having from 6 to 24 carbon atoms. As can be seen from the formula, at least one of $R_1$ or $R_2$ is in a position ortho to the hydroxyl group. The other alkyl group—i.e., $R_2$—is either (a) in the other ortho position to the hydroxyl group or (b) meta to the hydroxyl group, and para to the $R_1$ group. Although not so limited, the $R_1$ and $R_2$ groups are preferably branched alkyl groups such as t-butyl, isopropyl, 2-ethylhexyl, etc. It will be understood, however, that compounds possessing a 3-t-butyl-6-methyl-p-phenolic moiety or other similar structures are clearly contemplated.

In the formula given above, preferably "a" is 2 while $R_3$ is a linear alkyl group having from 4 to 10 carbon atoms, and $R_4$ is a linear alkyl group having from 6 to 12 carbon atoms. As noted above, compounds of Formula I, wherein $R_3$ and $R_4$, in the aggregate, contain from 14 to 24 carbon atoms, are liquids at temperatures about or below 0° C. but, because of their molecular weight, possess low volatility at elevated temperatures and accordingly can be used in host materials that are subject to elevated temperatures either during processing or in end use.

The compositions of the present invention are characterized in that at least one compound having the structure of Formula I is present in an amount of about 80% by weight or greater. Especially preferred compositions are characterized in that $R_3$ and $R_4$ contain, in the aggregate, 12 to 24 carbon atoms and said at least one compound is present in an amount of 95% by weight or greater.

The compounds forming the antioxidant compositions of the present invention and encompassed within Formula I can be prepared by transesterifying the phenol esters of Formula II with alcohols of Formula III at elevated temperatures in the presence of a suitable catalyst:

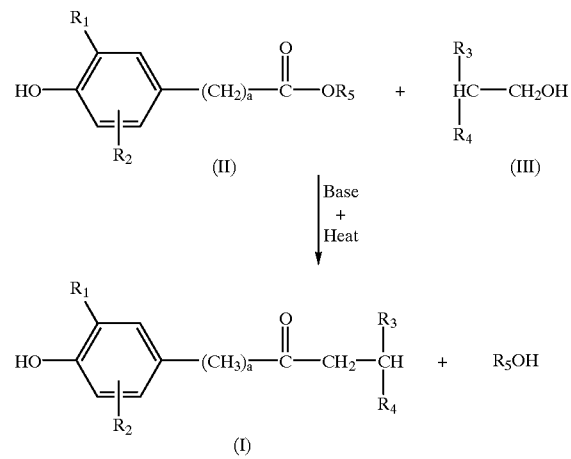

wherein $R_5$ is an alkyl group, preferably methyl or ethyl.

Transesterification reactions of the type under consideration to produce the antioxidants of the present invention are well known, as disclosed in U.S. Pat. No. 5,696,281 and standard textbooks of chemistry, and also in U.S. Pat. Nos. 4,228,297; 3,644,482; and 3,285,855, all of which are incorporated herein by reference for all purposes. The reaction can be carried out in a per se known manner, conveniently by adding one of the two educts to the second educt and thoroughly mixing both reactants, preferably excluding atmospheric oxygen. The reaction can be carried out in the presence of a solvent, typically toluene, xylene, or the like, or in the absence of a solvent. Reaction temperatures depend on the respective educts but will generally range from 50 to 250° C., preferably from 100 to 150° C. During the transesterification reaction, it is expedient to add customary transesterification catalysts to the reaction mixture. Exemplary of such catalysts are organic or inorganic bases such as lithium amide, lithium methoxide, or potassium hydroxide, or a Lewis acid such as dibutyltin oxide. Other catalysts such as alkyl titanates—e.g., isopropyl titanate-can also be employed.

The transesterification reactions are usually equilibrium reactions. To shift the equilibrium to the product side, it is therefore expedient to continuously remove a component that forms from the reaction mixture conveniently by distillative removal of the by-product alcohol—e.g., $R_5OH$. Another means of shifting the equilibrium consists of increasing the concentration of one or both reactants, preferably that of the alcohol. Other methods of preparing the antioxidants of the present invention are well known to those skilled in the art and are disclosed in standard textbooks of chemistry.

Generally, the alcohol educt used in the transesterification reaction of the present invention is a Guerbet alcohol having the Formula III shown above wherein $R_3$ and $R_4$ have the same significance as described with respect to Formula I. The alcohol educts of the present invention are defined as 2-alkyl-1-alkanols. Suitable Guerbet alcohols useful as the alcohol educt having Formula III are sold commercially under the trademark ISOFOL by CONDEA Chemie Company.

As noted above, the compounds of Formula I can be made to a high degree of purity, generally containing no more than three components. This is to be contrasted with prior art antioxidants, particularly liquid antioxidants, which typically have five or more components. Accordingly, the analysis of the antioxidants of the present invention is much easier and more accurate since there is a paucity of interfering extraneous components.

A myriad of host materials—e.g., organic materials or compositions containing organic materials—can be stabilized against thermal, oxidative, and/or actinic degradation using the antioxidants of the present invention. Non-limiting examples of such host materials include polymers of monoolefins, di-olefins, and mixtures of such polymers; copolymers of mono-olefins and di-olefins with each other or with other vinyl monomers; hydrocarbon resins (for example, $C_5$–$C_9$), including hydrogenated modifications thereof—e.g., tackifiers-and mixtures of polyalkylenes and starch; polystyrene; copolymers of styrene or alpha-methylstyrene with dienes or acrylic derivatives—e.g., styrene/butadiene; graft polymers of styrene or alpha-methylstyrene—e.g., styrene on butadiene; halogen-containing polymers such as polychloroprene, chlorinated rubbers, chlorinated or sulfochlorinated polyethylene; copolymers of ethylene and chlorinated ethylene; epichlorohydrin; homo- and copolymers, especially polymers of halogen-containing vinyl compounds, for example, polyvinyl chloride, polyvinylidene chloride, polyvinyl fluoride, polyvinylidene fluoride, as well as copolymers thereof such as vinyl chloride/vinylidene chloride, vinyl chloride/vinyl acetate, or vinylidene chloride/vinyl acetate copolymers; polymers derived from alpha-beta-unsaturated acids and derivatives thereof such as polyacrylates; polymers derived from unsaturated alcohols and amines of the acyl derivatives or acetals thereof; homopolymers and copolymers of cyclic ethers such as polyalkylene glycols; polyacetals; polyphenylene oxides and sulfides; polyurethanes derived from hydroxy-terminated polyethers, polyesters, etc.; polyamides and copolyamides; polyureas; polyesters; polycarbonates; polysulfones; cross-linked polymers derived from aldehydes—e.g., aldehydes and phenols; drying and non-drying alkyd resins; unsaturated polyester resins derived from copolyesters of saturated and unsaturated dicarboxylic acids with polyhydric alcohols; cross-linkable acrylic resins derived from substituted acrylates; natural polymers such as cellulose, rubber, gelatin, and chemically modified homologous derivatives thereof, for example, cellulose acetates, cellulose proprionates and cellulose butyrates, or the cellulose ethers such as methyl cellulose; blends of many of the aforementioned polymers; naturally occurring and synthetic organic materials that are pure monomeric compounds or mixtures of such compounds, as, for example, mineral oils, animal and vegetable fats, oils and waxes, or oils, fats, and waxes based on synthetic esters (e.g., phthalates, adipates, etc.); mixtures of synthetic esters with mineral oils in any weight ratios, typically those used in spinning compositions, as well as aqueous emulsions of such materials; aqueous emulsions of natural or synthetic rubber; lubricants and hydraulic fluids based on mineral or synthetic oils or mixtures thereof; polyols such as used in the production of polyurethanes, hydrocarbon materials such as gasoline, both natural and synthetic, diesel oil, fuel oil, cutting fluids; and surfactants, soaps, and personal care products such as hand lotions and skin preparations as disclosed, for example, in U.S. Pat. No. 5,821,206, incorporated herein by reference for all purposes.

The antioxidants of the present invention as exemplified by Formula I are particularly useful as antioxidants in host materials such as synthetic organic polymers, lubricating oils, polyols, and the like.

As will be recognized, the amount of antioxidant employed in the host material will vary depending upon the nature of the host material, the processing to which the host material is subjected, the end use of the host material, etc. In general, however, the antioxidant will be present in the host material in a stabilizing amount that can be determined from the host material, its processing, and its intended use. Generally, the antioxidant will be present in the host material in an amount of from about 0.001 to about 10% by weight, typically 0.02 to about 0.5% by weight, most preferably from about 0.025 to about 0.25% by weight.

The antioxidant compositions may be incorporated into the host material in a variety of methods depending upon the nature of the host material. For example, in the case of polymeric materials, the antioxidant compositions can be incorporated in master batches that are later further blended with more polymer and/or other additives to form a final desired end product. Since most of the antioxidant compositions are liquids at ambient temperature, they can be easily metered into host materials with great accuracy and furthermore, being liquids, can be more easily uniformly distributed throughout the host material.

To more fully illustrate the present invention, the following non-limiting examples and experimental data are presented.[1]

[1]All percents are by weight unless otherwise indicated.

EXAMPLE 1
(Preparation of Antioxidant Compositions)

The antioxidant compositions of the present invention were synthesized using standard methods of transesterification such as disclosed in "Alkylphenols," J. F. Lorenz, G. Lambeth, W. Sheffler, *Encyclopedia of Chemical Technology*, 4th Ed., Vol. 2, p. 122. In all cases, the methyl ester 3,5-di-tert-butyl-4-hydroxycinnamic acid was transesterified with a suitable Guerbet alcohol using 0.15 weight percent isopropyl titanate catalyst in a xylene medium. The three alcohols used were ISOFOL® 12 (2-butyl-1-octanol), ISOFOL® 16 (2-hexyl-1-decanol), and ISOFOL® 20 (2-octyl-1-dodecanol). The reaction was stirred and heated to 150° C. under nitrogen for three hours. During the reaction, methanol was continuously removed via azeotropic distillation. One mole of methanol was removed for every mole of the methyl ester used. The raw ester was purified by short path distillation or thin film evaporation after neutralization. To improve color, the ester product was stirred with 5% by weight tonsil clay and filtered.

There were thus produced three antioxidants identified as ISOFOL® 12 Ester, ISOFOL® 16 Ester, and ISOFOL® 20 Ester made from the three Guerbet, ISOFOL® branch alcohols described above. To determine purity of the antioxidants, a reverse phase high pressure liquid chromatography (HPLC) method was employed. In the latter method, a Spherisorb (ODS2) ($C_{18}$) column was used (4.6× 250 mm, 5μ). The eluent was a mixture of water and acetonitrile, which was initially 50% acetonitrile and was ramped to 100% acetonitrile over 15 minutes (1 ml/min). The eluent composition was maintained at 100% acetonitrile for the next 35 minutes, and the flow rate was increased to 1.5 ml/min. UV absorbency at 265 nm was monitored to determine the amount of material eluted. It was found that the HPLC chromatograms for the three antioxidants—i.e., ISOFOL® 12 Ester, ISOFOL® 16 Ester, and ISOFOL® 20 Ester—exhibited purities of 93.20%, 97.0%, and 97.70%, respectively, all of the antioxidants exhibiting only one major peak.

EXAMPLE 2

To demonstrate the low volatility of the liquid antioxidants of the present inventions, thermogravimetric analysis (TGA) was conducted using a dynamic scanning calorimeter (DSC). The products were heated at a rate of 20° C./min under nitrogen. In addition to the liquid antioxidants produced as per the present invention, TGA was also conducted on two other prior art liquid antioxidants. The prior art liquid antioxidants used differed from the structure of Formula I in that in one case (prior art antioxidant PA-1), the Guerbet alcohol residue was replaced with a $C_7$–$C_9$ alkyl grouping that is a mixture of linear and branched alkyls[2] and in the second case (prior art antioxidant PA-2), the Guerbet alcohol residue was replaced with a $C_{14}$–$C_{15}$ alkyl group that is a mixture of

[2]PA-1 is a composition containing greater than 5 components and 80% by weight of a compound having the formula:

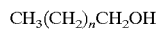

wherein n=5 to 7, and 20% by weight of a compound having the formula:

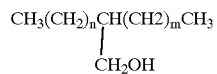

wherein n=0 to 5 and n+m=3 to 5. linear and branched alkyls.[3]

[3]PA-2 is a composition containing greater than 10 components and 50% by weight of a compound having the formula:

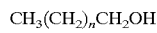

wherein n=12 to 13, and 50% by weight of a compound having the formula:

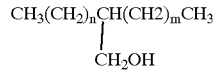

wherein n=0 to 10/11 and n+m=10/11. The result The result of the TGA analysis are shown in FIG. 1. As can be seen from FIG. 1, the volatility of the antioxidants decreases as the carbon chain length of the Guerbet alcohol residue increases. The 2-butyl octyl (ISOFOL® 12 Ester) and the 2-hexyl dodecyl (ISOFOL® 16 Ester) derivatives have similar volatility curves to the $C_{14}$–$C_{15}$ alkyl derivatives, but the volatility of the 2-octyl dodecyl (ISOFOL® 20 Ester) derivative was the lowest due to its molecular weight. In any event, as the data in FIG. 1 show, the volatility of the liquid antioxidants of the present invention compares quite favorably with prior art liquid antioxidants.

EXAMPLE 3

Figure 2:
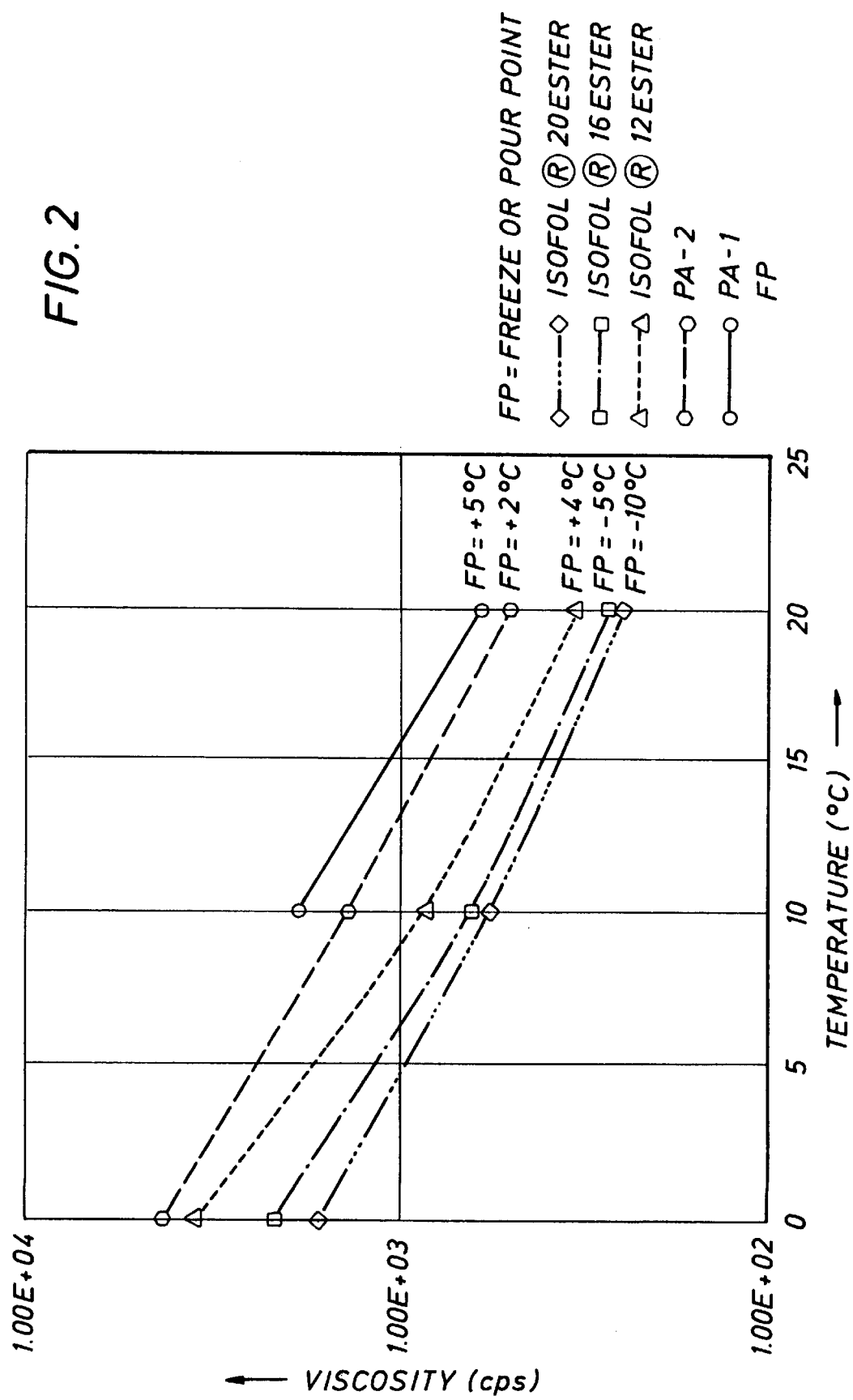
FIG. 2 is a graph comparing the low temperature viscosity of the antioxidant compositions of the present invention with prior art antioxidant compositions.

The three antioxidants of the present invention produced as per Example 1 and the comparative antioxidants PA-1 and PA-2 were tested for low temperature properties. The results are shown in FIG. 2. As can be seen from FIG. 2, the freezing points of the ISOFOL 16 and the ISOFOL 20 esters were less than 0° C. as compared with the freezing points of PA-1 and PA-2 antioxidants, which were both above 0° C. In general, the liquid antioxidants of the present invention had lower freezing points and lower viscosities at lower temperatures compared to the products (PA-1 and PA-2) made with the linear or oxo-type alcohols. Surprisingly, and as can be seen in FIG. 2, it was found that the viscosity and freeze point decrease with increasing carbon chain length of the Guerbet alcohol residue.

EXAMPLE 4

In this example, the antioxidants of the present invention and prior art antioxidants[4] were tested to determine their ability to retard degradation in a polymeric composition. A pipe grade suspension PVC resin was produced in a laboratory reactor. As is the custom with these types of polymerization, antioxidant is added during the final stages of polymerization prior to the removal of the resin from the reactor. The antioxidant performance was determined by the visible spectrum change after the PVC resin had been aged at 80° C. More specifically, the reduction in percent reflectivity at two dominant wavelengths (450 and 560 nm) is indicative of degradation and chromophore generation. The results are shown in Table 1. As can be seen in Table 1, the PVC stabilized with ISOFOL® 20 Ester exhibited the smallest reduction in percent reflectivity at both wavelengths. It is important to note that on the basis of active phenoxy equivalents, the ISOFOL® 20 Ester was used at 34% of the loading of the prior art low molecular weight antioxidant (Proprietary Alkylphenol). In both cases where antioxidant was present, the antioxidant was present in the PVC resin at a level of 0.02 weight percent.

[4]Also used was solid antioxidant wherein the Guerbet alcohol residue was replaced with a linear $C_{18}$ alkyl group.

EXAMPLE 5

The antioxidant compositions of the present invention produced as per Example 1, and prior art antioxidant compositions (PA-1 and PA-2) were incorporated into a flexible PVC wire and cable formulation and compared with a formulation having no antioxidants to see the effect, after aging, on physical parameters such as tensile strength and elongation. In all cases, the antioxidant was present in the formulation in an amount of 0.15 weight percent. In each case, 0.35 mm thick samples were aged in an oven for 14 days at 121° C. A 21-day study using the same conditions was also conducted to test the antioxidants under more stringent conditions. The results are shown in Table 2 below. As can be seen, in general the antioxidants of the present invention performed as well as the other liquid products, PA-1 and PA-2, as well as the solid antioxidant, PA-3.

TABLE 1

|  | Loading (wppm) | Phenoxy Equiv. (× $10^{-3}$ moles) | 450 nm % Reflectance Reduction | | | 560 nm % Reflectance Reduction | | |
| --- | --- | --- | --- | --- | --- | --- | --- | --- |
|  |  |  | 30 minutes @ 80° C. | 60 minutes @ 80° C. | 90 minutes @ 80° C. | 30 minutes @ 80° C. | 60 minutes @ 80° C. | 90 minutes @ 80° C. |
| PVC Resin | 0 | 0 | 1.17 | 3.99 | 7.64 | 1.13 | 4.94 | 9.92 |
| Proprietary Alkylphenol | 192 | 15.2 | 2.41 | 2.85 | 3.80 | 4.00 | 4.70 | 5.95 |
| PA-2 | 200 | 6.3 | 1.31 | 2.52 | 3.98 | 1.82 | 3.59 | 4.98 |
| ISOFOL ® 12 Ester | 202 | 6.8 | 1.95 | 2.35 | 3.23 | 3.05 | 3.64 | 4.70 |
| ISOFOL ® 16 Ester | 199 | 6.0 | 1.92 | 2.33 | 3.50 | 2.77 | 3.36 | 4.83 |
| ISOFOL ® 20 Ester | 197 | 5.3 | 1.62 | 1.90 | 3.01 | 2.48 | 2.91 | 4.28 |
| PA-3 | 213 | 6.0 | 1.33 | 2.68 | 4.90 | 1.22 | 3.11 | 5.74 |

TABLE 2

|  | No Antioxidant | ISOFOL ® 12 Ester | ISOFOL ® 16 Ester | ISOFOL ® 20 Ester | Linear 18 Ester (PA-3) | Branched 7,9 Ester (PA-1) | Branched 14,15 Ester (PA-2) |
| --- | --- | --- | --- | --- | --- | --- | --- |
| Unaged Tensile Strength, psi | 2957 | 2927 | 2815 | 2975 | 3001 | 2938 | 2709 |
| Unaged Elongation, % | 456 | 455 | 447 | 468 | 459 | 460 | 442 |
| Oven Aged 14 Day @ 121° C. |  |  |  |  |  |  |  |
| Tensile Strength, psi | 3006 | 2938 | 3102 | 3000 | 3027 | 2993 | 2972 |
| Elongation, % | 401 | 426 | 414 | 416 | 418 | 414 | 418 |
| Retention Tensile Strength, % | 102 | 100 | 110 | 101 | 101 | 102 | 110 |
| Retention Elongation, % | 88 | 94 | 98 | 89 | 91 | 90 | 95 |

TABLE 2-continued

|  | No Antioxidant | ISOFOL® 12 Ester | ISOFOL® 16 Ester | ISOFOL® 20 Ester | Linear 18 Ester (PA-3) | Branched 7,9 Ester (PA-1) | Branched 14,15 Ester (PA-2) |
| --- | --- | --- | --- | --- | --- | --- | --- |
| Oven Aged 21 day @ 121° C. |  |  |  |  |  |  |  |
| Tensile Strength, psi | 2905 | 3033 | 3198 | 3009 | 3227 | 3207 | 3085 |
| Elongation, % | 320 | 336 | 357 | 360 | 348 | 393 | 370 |
| Retention Tensile Strength, % | 98 | 104 | 114 | 101 | 108 | 109 | 114 |
| Retention Elongation, % | 70 | 74 | 80 | 77 | 76 | 85 | 84 |

EXAMPLE 6

This example demonstrates the ability of the antioxidants of the present invention to prevent degradation of other host materials such as polyols. Polyols are commonly used in the production of foamed polyurethane. The polyol used for testing in this example was VORANOL® 3071, produced by the Dow Chemical Company. VORANOL® 3071 is a polyether polyol used in the production of flexible polyurethane foam. Each sample contained 0.15 weight percent of the respective antioxidant. Testing of the polyols containing the antioxidants, as well as the polyol with no antioxidant was conducted by TGA, oxidation onset temperatures of the antioxidant-containing polyols being conducted using DSC. A ramp rate of 5° C./min to 200° C. was used in the presence of oxygen. The results are shown in Table 3 below. As can be seen, the antioxidants of the present invention produced per Example 1 increase the onset of polyol oxidation by approximately 10° C. compared to the polyol with no antioxidants. These results are comparable to other prior art antioxidants—i.e., PA-1, PA-2, and PA-3—commonly used to stabilize polyols.

TABLE 3

| Additive | Oxidation Onset Temperature, ° C. |
| --- | --- |
| No Antioxidant | 163.2 |
| Branched 7,9 Ester (PA-1) | 173.4 |
| ISOFOL ® 12 Ester | 171.0 |
| ISOFOL ® 16 Ester | 171.5 |
| ISOFOL ® 20 Ester | 172.0 |
| Branched 14, 15 Ester (PA-2) | 173.8 |
| Linear 18 Ester (PA-3) | 172.2 |

Standard Deviation = ±1 degree

The antioxidants of the present invention possess several unique qualities. For one, and with respect to the antioxidants per Formula I wherein the total number of carbon atoms in the Guerbet alcohol residue contain 14 to 24 carbon atoms, the products are liquid at about or below 0° C. Some of the antioxidants of the present invention are the highest molecular weight hindered phenols that are liquid, yet their antioxidant performance is similar to other liquid hindered antioxidants of lower molecular weight, which inherently makes the latter more volatile with higher freezing points. A decided advantage of the antioxidants of the present invention is that they can be made in a high degree of purity, which makes them easier to analyze at low levels in a host material. At these low levels, these antioxidants maintain their antioxidant efficiency. Additionally, the low viscosity and low freeze point properties of the liquid antioxidants of the present invention are also advantageous for handling at ambient temperatures in a plant setting since they can be readily metered into the host material.

The foregoing description and examples illustrate selected embodiments of the present invention. In light thereof, variations and modifications will be suggested to one skilled in the art, all of which are in the spirit and purview of this invention.

What is claimed is:

1. An antioxidant composition comprising a compound having the formula:

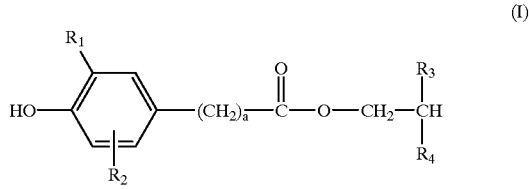

(I)

wherein $R_1$ and $R_2$ are each hydrocarbon groups having from 1 to 8 carbon atoms, a is from 1 to 3, $R_3$ is a linear alkyl group having from 6 to 8 carbon atoms, $R_4$ is a linear alkyl group having from 10 to 12 carbon atoms, the

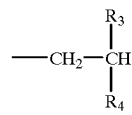

grouping being the hydrocarbyl residue of a β-branched Guerbet alcohol, and wherein said at least one compound is present in said composition in an amount of 80% or greater by weight, said at least one compound being liquid in a temperature range of from about 0 to −10° C.

2. The composition of claim 1 wherein a is 2.

3. The composition of claim 1 wherein $R_1$ and $R_2$ are branched chain alkyl groups.

4. The composition of claim 3 wherein $R_1$ and $R_2$ are t-butyl groups.

* * * * *